US012532923B2

(12) United States Patent
Ma

(10) Patent No.: US 12,532,923 B2
(45) Date of Patent: Jan. 27, 2026

(54) TOE SEPARATION CORRECTION SOCK

(71) Applicant: Dongguan Xili Technology Co., Ltd, Guangdong (CN)

(72) Inventor: Qingli Ma, Guangdong (CN)

(73) Assignee: Dongguan Xili Technology Co., Ltd, Dongguan (CN)

( * ) Notice: Subject to any disclaimer, the term of this patent is extended or adjusted under 35 U.S.C. 154(b) by 205 days.

(21) Appl. No.: 18/616,122

(22) Filed: Mar. 25, 2024

(65) Prior Publication Data

US 2024/0324697 A1 Oct. 3, 2024

(30) Foreign Application Priority Data

Mar. 31, 2023 (CN) ......................... 202320683083.3

(51) Int. Cl.
*A41B 11/00* (2006.01)
*A61F 5/01* (2006.01)

(52) U.S. Cl.
CPC ............ *A41B 11/004* (2013.01); *A61F 5/019* (2013.01)

(58) Field of Classification Search
CPC ....... A41B 11/004; A41B 11/00; A61F 5/019; A61F 5/01; A61F 5/00
See application file for complete search history.

(56) References Cited

FOREIGN PATENT DOCUMENTS

| | | | | | |
|---|---|---|---|---|---|
| CN | 210250180 U | * | 4/2020 | | |
| DE | 202018102884 U1 | * | 5/2018 | ........... | A41B 11/004 |
| KR | 20210103872 A | * | 8/2021 | ............. | A61F 5/019 |
| TW | M622313 U | * | 1/2022 | | |
| WO | WO-2017051981 A1 | * | 3/2017 | ............... | A61F 5/01 |

* cited by examiner

*Primary Examiner* — Tarla R Patel

(57) ABSTRACT

A toe separation correction sock includes a toe separation sock and an elastic toe separation module, wherein a front end of the toe separation sock includes a hallux sleeving part and a second sleeving part, the second sleeving part is used for sleeving remaining four toes except for a hallux, the elastic toe separation module includes a carrier assembly and a filling assembly, the carrier assembly includes an elastic sleeve, the elastic sleeve is fixedly arranged between the hallux sleeving part and the second sleeving part, the filling assembly includes a plurality of filling blocks, and any filling block is capable of being contained in an inner cavity of the elastic sleeve. The elastic toe separation module is arranged on an outer side of the toe separation sock, then wearing and using of the toe separation sock and the elastic toe separation module are conveniently achieved.

13 Claims, 6 Drawing Sheets

TOE SEPARATION CORRECTION SOCK

CROSS-REFERENCE TO RELATED APPLICATIONS

The present disclosure claims priority of the Chinese patent application No. 202320683083.3 filed on Mar. 31, 2023, the entire content of which is incorporated herein by reference.

TECHNICAL FIELD

The present disclosure relates to the technical field of socks, in particular to a toe separation correction sock.

BACKGROUND ART

Hallux valgus is a common foot problem, there are various reasons, such as congenital heredity and compressed deformation of halluces caused by long-term wearing of narrow-lasted shoes or high heels, and common flat feet are also one of the reasons. Slight hallux valgus can be relieved with the help of various correction apparatuses, while severe cases can only be treated through surgery.

A novel patent No. TW110212055U from Taiwan, China has disclosed a hallux correction sock, including a sock body, a fixing part, and at least one adjusting part. The sock body is provided with a hallux part and a four-toe part. A containing region is formed outside the sock body and located between the hallux part and the four-toe part. The fixing part is located in the containing region and connected with the hallux part. The at least one adjusting part is located in the containing region and detachably combined with the fixing part. In the above technical solution, one side of the fixing part is fixedly connected with the hallux part, the other side thereof is connected with the adjusting part, the adjusting part is relatively separated from opposite sides of the four-toe part, therefore, in actual application, when a hallux moves up and down relative to a second toe, the adjusting part may disengage from the containing region; and the pressed adjusting part and fixing part will rebound to deform after the adjusting part disengages from the containing region since both the adjusting part and the fixing part are made of plastic, the adjusting part and fixing part that rebound to deform become larger, so that the adjusting part cannot normally return into the containing region after the hallux returns to an original position again, and therefore a correction effect of the adjusting part is lost.

SUMMARY

The present disclosure aims at providing a toe separation correction sock. Two sides of an elastic sleeve in the correction sock are fixedly connected with a hallux sleeving part and a second sleeving part respectively, and filling blocks are clamped in the elastic sleeve, so as to be effectively prevented from disengaging from a position between a hallux and a second toe when the hallux moves up and down, thereby ensuring a continuous correction function of the correction sock.

A technical solution adopted for solving the technical problem of the present disclosure is as follows: A toe separation correction sock, includes a toe separation sock and an elastic toe separation module, a front end of the toe separation sock includes a hallux sleeving part and a second sleeving part, the second sleeving part is used for sleeving four toes except for the hallux, the elastic toe separation module includes a carrier assembly and a filling assembly, the carrier assembly includes an elastic sleeve, the elastic sleeve is fixedly arranged between the hallux sleeving part and the second sleeving part, the filling assembly includes a plurality of filling blocks, and any filling block can be contained in an inner cavity of the elastic sleeve.

Preferably, a filling opening is formed in an upper portion of the elastic sleeve, a cross section area of the filling opening is less than a cross section area of the cavity of the elastic sleeve, and a cross section area of any filling block is greater than the cross section area of the filling opening.

Furthermore, the carrier assembly further includes an annular reinforcing tape, and the annular reinforcing tape is fixedly arranged on a left side of the elastic sleeve and used for fixedly sleeving the hallux sleeving part.

Furthermore, the carrier assembly further includes a left square bracket-shaped reinforcing tape, the left square bracket-shaped reinforcing tape is fixedly arranged on a right side of the elastic sleeve, and a side wall, away from the elastic sleeve of the left square bracket-shaped reinforcing tape is fixedly connected with a corresponding outer side wall of the second sleeving part.

Furthermore, the elastic sleeve, the annular reinforcing tape and the left square bracket-shaped reinforcing tape are all made of silica gel.

Furthermore, the filling assembly includes three filling blocks, and the three filling blocks are a first filling block, a second filling block and a third filling block respectively.

Furthermore, the first filling block, the second filling block and the third filling block are all elastomers.

Furthermore, both thicknesses and hardnesses of the first filling block, the second filling block and the third filling block are sequentially increased, cross sections of the first filling block and the second filling block are oval, and a cross section of the third filling block is triangular.

Furthermore, the second sleeving part is in a single-cylinder shape, and when the four toes are sleeved with the second sleeving part, an upper extension end of the left square bracket-shaped reinforcing tape is located above a second toe, and a lower extension end of the left square bracket-shaped reinforcing tape is located below the second toe.

The present disclosure has the beneficial effects that the toe separation correction sock is simple in structure and convenient to process and manufacture; the two sides of the elastic sleeve are fixedly connected with side walls of the hallux sleeving part and the second sleeving part respectively, so that the elastic sleeve swings along with the hallux up and down to a certain degree when the hallux swings up and down relative to the second toe, and when the elastic sleeve swings up and down to a certain degree, the filling blocks can be effectively prevented from disengaging from the elastic sleeve since they are clamped in the elastic sleeve, so as to still ensure the correction function of the correction sock when the hallux moves up and down, thereby improving the practicality of the correction sock; the annular reinforcing tape and the left square bracket-shaped reinforcing tape are fixedly connected with corresponding sock body, so that the stability and fixation of the elastic sleeve between the hallux sleeving part and the second sleeving part can be improved, thereby improving the durability of the correction socks; both the thicknesses and hardnesses of the first filling block, the second filling block and the third filling block are different, so that different correction requirements of users can be met, thereby improving flexibly application of the correction socks; and the filling blocks are the elastomers, so that they can be smoothly put in the cavity of the elastic sleeve through the filling opening after being compressed, and the cross sections of the filling blocks are larger than the cross section of the filling opening after the filling blocks rebound to restore in the cavity, so that the filling blocks can be effectively prevented from being exposed out of the filling opening, laying a foundation for continuously ensuring the correction function of the correction sock.

BRIEF DESCRIPTION OF THE DRAWINGS

In order to more clearly explain the embodiments of the present disclosure or the technical solutions of the prior art, the drawings needed in the description of the embodiments or the prior art will be briefly described below. Apparently, the drawings in the following description are part of preferred embodiments of the present disclosure. For those ordinarily skilled in the art, other drawings can be obtained in accordance with these drawings without involving any inventive efforts.

In the drawings.

1—toe separation sock, 2—annular reinforcing tape, 3—elastic sleeve, 4—left square bracket-shaped reinforcing tape, 5—filling block, 6—inner cavity, 7—hallux sleeving part, 8—second sleeving part, 9—carrier assembly, 10—first filling block, 11—second filling block, and 12—third filling block.

DETAILED DESCRIPTION OF THE EMBODIMENTS

The technical solutions in the embodiments of the present disclosure will be clearly and completely described below with reference to the specific embodiments and FIGS. 1-10. Apparently, the described embodiments are merely part of the preferred embodiments, rather than all embodiments of the present disclosure. Those skilled in the art can make similar transformations without departing from the content of the present disclosure, so that the present disclosure is not limited by specific embodiments as disclosed below.

Figure 1:
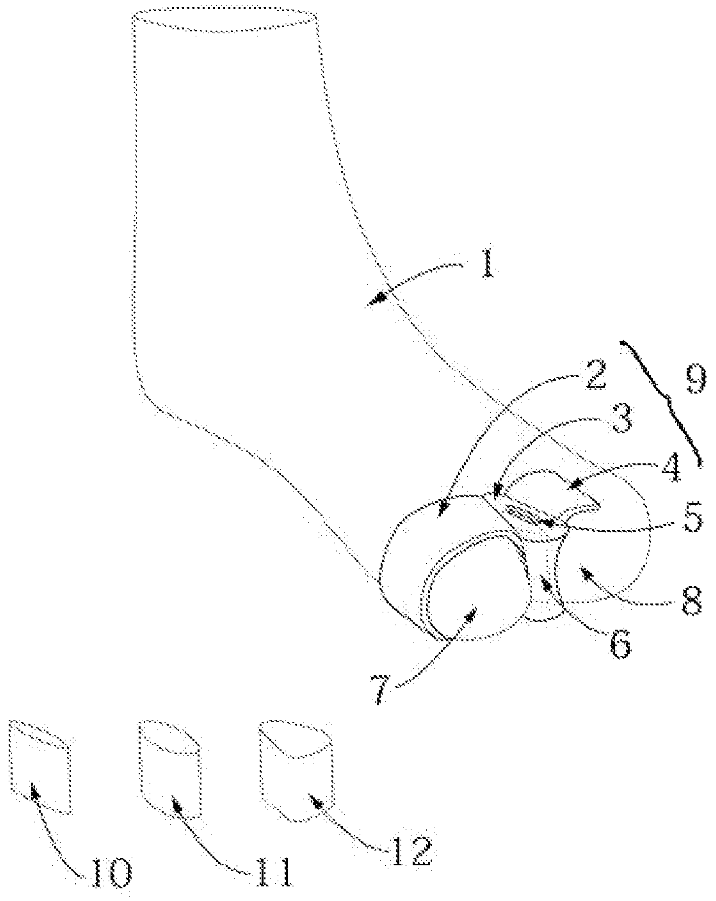
FIG. 1 is a schematic diagram of an overall structure according to a first embodiment of the present disclosure.
Figure 2:
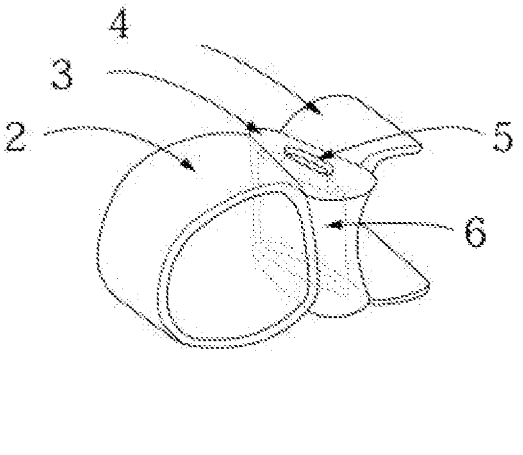
FIG. 2 is a schematic structural diagram of a carrier assembly.
Figure 3:
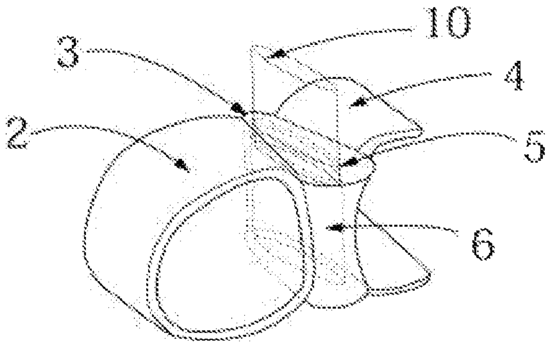
FIG. 3 is a schematic diagram showing a state in which a filling opening is expanded by a filling block.
Figure 4:
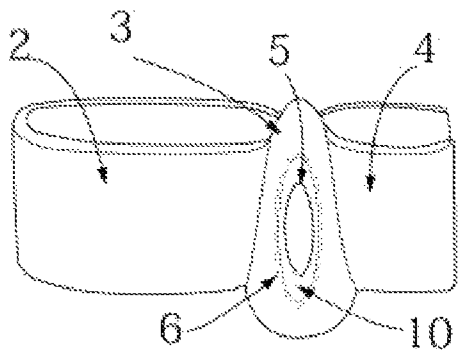
FIG. 4 is a top view of an elastic toe separation module.
Figure 5:
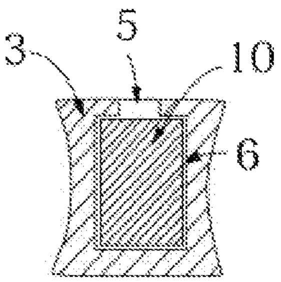
FIG. 5 is a longitudinal section diagram showing relative distribution of filling blocks and an elastic sleeve.
Figure 6:
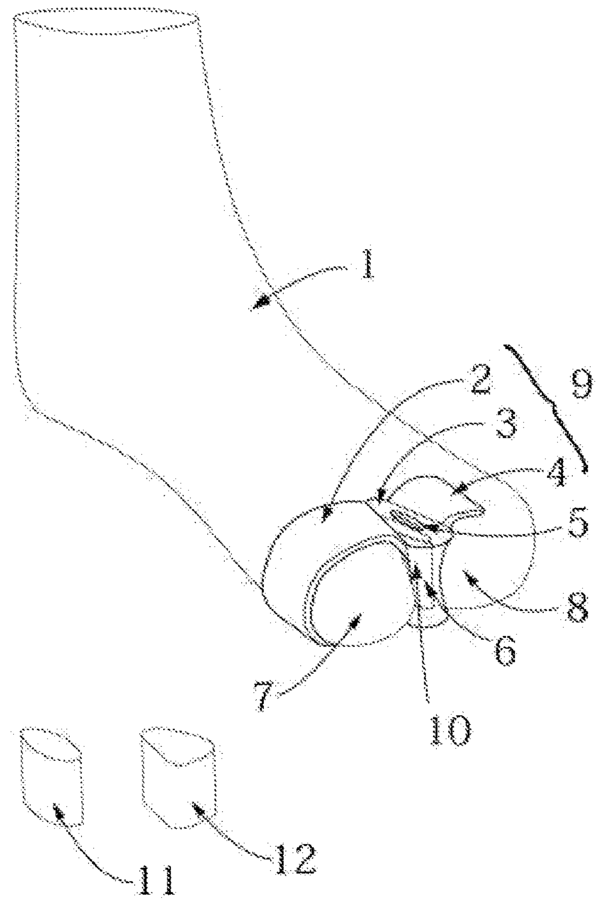
FIG. 6 is a schematic diagram showing a first application state of a first embodiment of the present disclosure.
Figure 7:
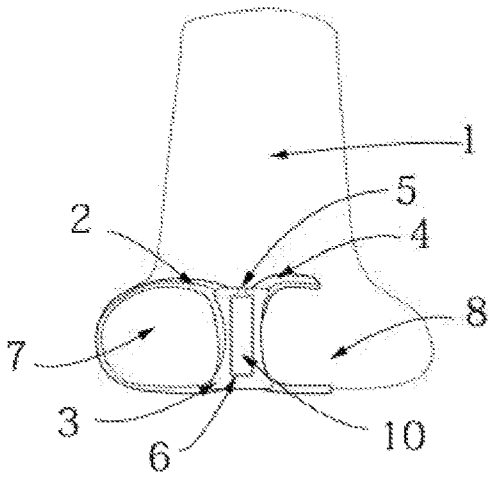
FIG. 7 is a front view showing a first application state of a first embodiment of the present disclosure.
Figure 8:
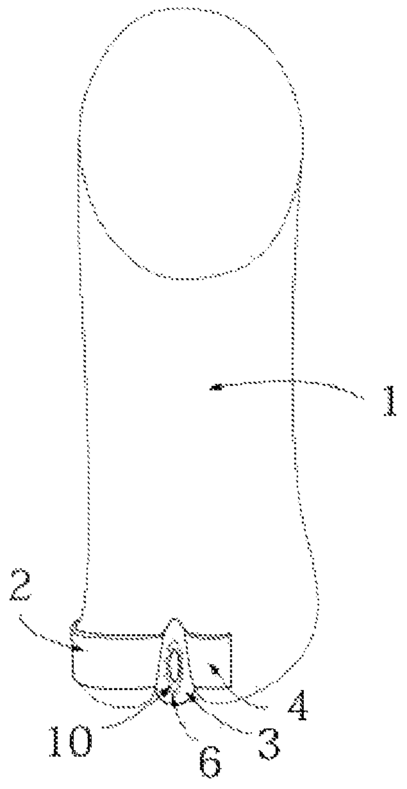
FIG. 8 is a top view showing a first application state of a first embodiment of the present disclosure.
Figure 9:
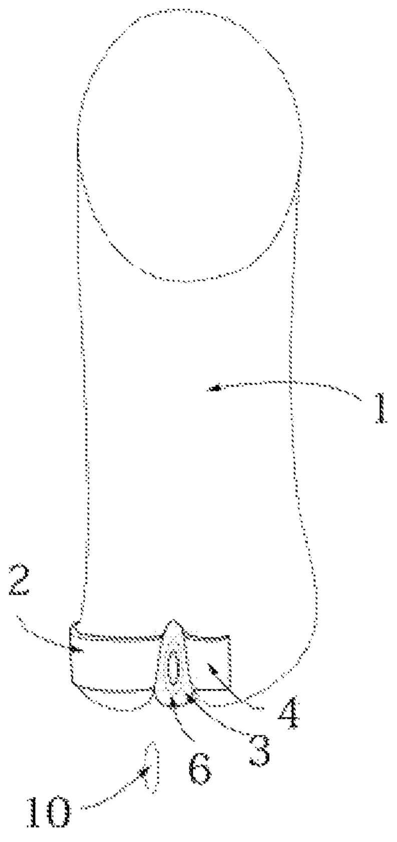
FIG. 9 is a top view showing a distribution state of filling blocks that are not filled in an elastic sleeve in a first embodiment of the present disclosure.
Figure 10:
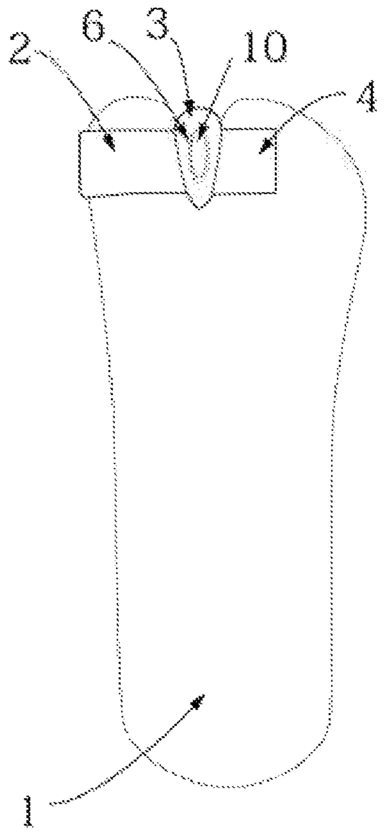
FIG. 10 is a bottom view showing a first application state of a first embodiment of the present disclosure.

The present disclosure provides a toe separation correction sock (as shown in FIG. 1), including a toe separation sock 1 and an elastic toe separation module. In the embodiment, a sock top of the toe separation sock 1 is higher than an ankle, but is not limited thereto, and it may also be lower than the ankle, such as heights and shapes of common boat socks. A front end of the toe separation sock 1 includes a hallux sleeving part 7 and a second sleeving part 8, the hallux sleeving part 7 is used for sleeving a hallux, the second sleeving part 8 is used for sleeving four toes except the hallux, and the hallux can be isolated from a second toe by means of the hallux sleeving part 7 and the second sleeving part 8. The elastic toe separation module includes a carrier assembly 9 and a filling assembly, the carrier assembly 9 includes an elastic sleeve 3, the elastic sleeve 3 is fixedly arranged between the hallux sleeving part 7 and the second sleeving part 8, and the elastic sleeve 3 can be fixedly connected with corresponding portions of the hallux sleeving part 7 and the second sleeving part 8 in a pasted manner. The filling assembly includes a plurality of filling blocks, and any filling block can be contained in an inner cavity 6 of the elastic sleeve 3. The filling blocks have a certain volume, and the filling blocks can push a front end of the hallux outwards when located between the hallux and the second toe, which is conducive to correction for hallux valgus.

In the above embodiment, in order to conveniently allow the filling blocks to be stably clamped in the elastic sleeve 3 to prevent the filling blocks from jumping out of the elastic sleeve 3, the elastic sleeve 3 is designed into a cylindrical structure with a closed bottom, a filling opening 5 is formed in an upper portion of the elastic sleeve 3, a cross section area of the filling opening 5 of the elastic sleeve 3 is less than a cross section area of the cavity of the elastic sleeve 3, a cross section area of any filling block is greater than the cross section area of the filling opening, the filling opening 5 may be expanded or contracted due to the elasticity of the elastic sleeve 3, when it is necessary to put the filling blocks in the elastic sleeve 3, the filling opening 5 may be expanded properly, then the filling blocks are put in the cavity 6 in the elastic sleeve 3, after the filling blocks are completely put in the cavity 6, the filling opening 5 is retracted to an original state, as a result, the filling blocks are effectively prevented from jumping out of the filling opening 5 by blocking the filling blocks by the upper portion of the elastic sleeve 3 since cross sections of the filling blocks are greater than a cross section of the filling opening 5.

In order to conveniently improve the fixation and stability of the elastic sleeve 3 between the hallux sleeving part 7 and the second sleeving part 8, a second specific embodiment showing the connection between the elastic sleeve 3 and the hallux sleeving part 7, as well as the elastic sleeve and the second sleeving part 8 is proposed. Here, the carrier assembly 9 further includes an annular reinforcing tape 2, the annular reinforcing tape 2 is fixedly arranged on a left side of the elastic sleeve 3 and used for fixedly sleeving the hallux sleeving part 7, and the connection stability of the left side of the elastic sleeve 3 and the hallux sleeving part 7 can be improved due to a large fixed contact area between the annular reinforcing tape 2 and the hallux sleeving part 7. Furthermore, on this basis, the carrier assembly 9 may further include a left square bracket-shaped reinforcing tape 4, the left square bracket-shaped reinforcing tape 4 is fixedly arranged on a right side of the elastic sleeve 3, a side wall, away from the elastic sleeve 3, of the left square bracket-shaped reinforcing tape 4 is fixedly connected with a corresponding outer side wall of the second sleeving part 8, the connection stability of the right side of the elastic sleeve 3 and the second sleeving part 8 can be improved due to a large contact area between the left square bracket-shaped reinforcing tape 4 and the second sleeving part 8, and the annular reinforcing tape 2 and the left square bracket-shaped reinforcing tape 4 can be fixedly connected with corresponding sock body in a pasted manner.

In order to improve the flexibility of the carrier assembly to conveniently improve the use comfort of the correction sock, the elastic sleeve 3, the annular reinforcing tape 2 and the left square bracket-shaped reinforcing tape 4 are all made of silica gel.

Furthermore, in order to meet different correction requirements of users, the filling assembly includes three filling blocks, and the three filling blocks are a first filling block 10, a second filling block 11 and a third filling block 12 respectively. In order to ensure certain compression elasticity of each filling block to ensure durability thrust to the hallux and the second toe, the first filling block 10, the second filling block 11 and the third filling block 12 are all elastomers, both thicknesses and hardnesses of the first filling block 10, the second filling block 11 and the third filling block 12 are sequentially increased, and the higher the thicknesses and hardnesses of the filling blocks, the greater the supporting and isolating effects achieved by the same. The thicknesses and hardnesses of the filling blocks can be determined by those skilled in the art through a finite number of experiments based on selected specific processing materials. In the embodiment, the filling blocks may be made from plastic or silica gel via processing, meanwhile, cross sections of the first filling block 10 and the second filling block 11 are oval, a cross section of the third filling block 12 is triangular, and one top end of the third filling block 12 is directed to a toe root when the third filling block 12 is used for isolation.

In actual application, the second sleeving part 8 may be in a single-cylinder shape or double-cylinder shape or three-cylinder shape or four-cylinder shape, and when the second sleeving part 8 is in the single-cylinder shape, and after the four toes are sleeved with the second sleeving part 8, an upper extension end of the left square bracket-shaped reinforcing tape 4 is located above the second toe, and a lower extension end of the left square bracket-shaped reinforcing tape 4 is located below the second toe.

In the present disclosure, terms "front", "back", "top", "bottom", "left" and "right" are all relative positions for convenience in describing positional relationships, and thus are not to be construed as limiting the scope of protection as absolute positions.

Other than the technical features in the specification, all the descriptions are technologies known to those skilled in the art.

The preferred implementations and embodiments of the present disclosure are described in detail above with reference to the accompanying drawings, however, the present disclosure is not limited to the above implementations and embodiments. Those ordinarily skilled in the art can also make several improvements and modifications without departing from the concept of the present disclosure, and these improvements and modifications should also fall within the scope of protection of the present disclosure.

The invention claimed is:

1. A toe separation correction sock, comprising a toe separation sock and an elastic toe separation module, wherein a front end of the toe separation sock comprises a hallux sleeving part and a second sleeving part, the second sleeving part is used for sleeving four toes except for a hallux, the elastic toe separation module comprises a carrier assembly and a filling assembly, the carrier assembly comprises an elastic sleeve, the elastic sleeve is fixedly arranged between the hallux sleeving part and the second sleeving part, the filling assembly comprises a plurality of filling blocks, and any filling block is capable of being contained in an inner cavity of the elastic sleeve wherein the carrier assembly further comprises an annular reinforcing tape, and the annular reinforcing tape is fixedly arranged on a left side of the elastic sleeve and used for fixedly sleeving the hallux sleeving part; wherein the carrier assembly further comprises a left square bracket-shaped reinforcing tape, the left square bracket-shaped reinforcing tape is fixedly arranged on a right side of the elastic sleeve, and a side wall, away from the elastic sleeve of the left square bracket-shaped reinforcing tape is fixedly connected with a corresponding outer side wall of the second sleeving part and wherein the second sleeving part is in a single-cylinder shape, and after the four toes are sleeved with the second sleeving part, an upper extension end of the left square bracket-shaped reinforcing tape is located above a second toe, and a lower extension end of the left square bracket-shaped reinforcing tape is located below the second toe.

2. The toe separation correction sock according to claim 1, wherein a filling opening is formed in an upper portion of the elastic sleeve, a cross section area of the filling opening is less than a cross section area of the cavity of the elastic sleeve, and a cross section area of any filling block is greater than the cross section area of the filling opening.

3. The toe separation correction sock according to claim 2, wherein the carrier assembly further comprises an annular reinforcing tape, and the annular reinforcing tape is fixedly arranged on a left side of the elastic sleeve and used for fixedly sleeving the hallux sleeving part.

4. The toe separation correction sock according to claim 1, wherein the elastic sleeve, the annular reinforcing tape and the left square bracket-shaped reinforcing tape are all made of silica gel.

5. The toe separation correction sock according to claim 4, wherein the second sleeving part is in a single-cylinder shape, and after the four toes are sleeved with the second sleeving part, an upper extension end of the left square bracket-shaped reinforcing tape is located above a second toe, and a lower extension end of the left square bracket-shaped reinforcing tape is located below the second toe.

6. The toe separation correction sock according to claim 4, wherein the filling assembly comprises three filling blocks, and the three filling blocks are a first filling block, a second filling block and a third filling block respectively.

7. The toe separation correction sock according to claim 6, wherein the second sleeving part is in a single-cylinder shape, and after the four toes are sleeved with the second sleeving part, an upper extension end of the left square bracket-shaped reinforcing tape is located above a second toe, and a lower extension end of the left square bracket-shaped reinforcing tape is located below the second toe.

8. The toe separation correction sock according to claim 6, wherein the first filling block, the second filling block and the third filling block are all elastomers.

9. The toe separation correction sock according to claim 8, wherein the second sleeving part is in a single-cylinder shape, and after the four toes are sleeved with the second sleeving part, an upper extension end of the left square bracket-shaped reinforcing tape is located above a second toe, and a lower extension end of the left square bracket-shaped reinforcing tape is located below the second toe.

10. The toe separation correction sock according to claim 8, wherein thicknesses of the first filling block, the second filling block and the third filling block are sequentially increased, cross sections of the first filling block and the second filling block are oval, and a cross section of the third filling block is triangular.

11. The toe separation correction sock according to claim 10, wherein the second sleeving part is in a single-cylinder shape, and after the four toes are sleeved with the second sleeving part, an upper extension end of the left square bracket-shaped reinforcing tape is located above a second toe, and a lower extension end of the left square bracket-shaped reinforcing tape is located below the second toe.

12. The toe separation correction sock according to claim 10, wherein hardnesses of the first filling block, the second filling block and the third filling block are sequentially increased.

13. The toe separation correction sock according to claim 12, wherein the second sleeving part is in a single-cylinder shape, and after the four toes are sleeved with the second sleeving part, an upper extension end of the left square bracket-shaped reinforcing tape is located above a second toe, and a lower extension end of the left square bracket-shaped reinforcing tape is located below the second toe.

* * * * *